United States Patent [19]

Hughes et al.

[11] 4,212,795
[45] Jul. 15, 1980

[54] CYCLIZATION OF PEPTIDES

[75] Inventors: John L. Hughes, Kankakee; Jay K. Seyler, Bourbonnais; Robert C. Liu, Kankakee, all of Ill.

[73] Assignee: Armour Pharmaceutical Company, Kankakee, Ill.

[21] Appl. No.: 960,229

[22] Filed: Nov. 13, 1978

[51] Int. Cl.² ............................................ C07C 103/52
[52] U.S. Cl. ........................ 260/112.5 T; 260/112.5 S; 260/112.5 R
[58] Field of Search .................... 260/112.5 S, 112.5 T

[56] References Cited

U.S. PATENT DOCUMENTS

| | | | |
|---|---|---|---|
| 3,929,758 | 12/1975 | Hughes et al. | 260/112.5 S |
| 3,988,309 | 10/1976 | Matsuda et al. | 260/112.5 T |
| 4,033,940 | 7/1977 | Hughes et al. | 260/112.5 S |

Primary Examiner—Delbert R. Phillips
Attorney, Agent, or Firm—Carl C. Batz

[57] ABSTRACT

The synthesis of a disulfide cyclic peptide by preparing an intermediate peptide containing two cysteine moieties, each of which is protected by an n-alkylthio group, or when one of such moieties is in an amino terminal position, this one moiety may be protected by a cysteine group while the other is protected by an n-alkylthio group, and placing such intermediate peptide in a solution substantially free of oxygen and preferably at a pH of from 5 to 10 until rearrangement has taken place, to yield a cyclic disulfide peptide. The disclosure also embraces said intermediate peptides as new compounds and the processes by which they are prepared.

19 Claims, No Drawings

CYCLIZATION OF PEPTIDES

This invention pertains to cyclization of peptides and more particularly to methods for treating peptides containing a cysteine residue within the amino acid sequence and a cystine residue at the amino terminal end to produce a disulfide bond between such residues and so form a ring structure. Such methods are useful in the synthesis of peptides which have biological activity and which are useful in the treatment of certain diseases in animals and man.

The invention pertains also to intermediate peptides which are precursors of cyclic disulfide peptides and to the preparation of such intermediate peptides.

BACKGROUND

Many peptides are known which are biologically active and are useful in the treatment of diseases and which contain a disulfide ring. Calcitonins, which are useful in the treatment of Paget's disease, contain a ring structure involving cysteine groups at the 1st and 7th positions in their amino acid chains. Oxytocin is useful for the therapeutic induction or stimulation of labor in humans and animals and also to control postpartum uterine bleeding. It contains a disulfide ring structure between the cysteine groups at positions 1 and 6 in its amino acid chain. Vasopressin and its analog lypressin are used as antidiuretic drugs in man and contain disulfide ring structures between the cysteine groups at positions 1 and 6 in their amino acid sequences (handbook of Biochemistry, pages C-164 to C-188).

Although the kind of sequence of the amino acid groups for the calcitonins, oxytocin, vasopressin, and other such naturally occurring peptides may vary depending upon the species from which they are obtained, all such peptides which are originally obtained from natural sources, such as by extraction from the glands of humans, domestic animals, fishes, frogs, or reptiles, contain the ring structure referred to above. The amino acid sequence of some known biologically active peptides containing cysteine groups joined by disulfide bonds in a ring structure are given in Table I.

Typical Peptides Containing Cysteine Ring Structure

Oxytocin:
H—CYS—TYR—ILE—GLN—ASN—CYS—PRO—LEU—GLY—NH$_2$

Vasopressin:
H—CYS—TYR—PHE—GLN—ASN—CYS—PRO—ARG—GLY—NH$_2$

Somatosatin:
H—CYS—SER—ASN—LEU—SER—THR—CYS—VAL—LEU—GLY—
LYS—LEU—SER—GLN—GLU—LEU—HIS—LYS—LEU—GLN—
THR—TYR—PRO—AGR—THR—ASP—VAL—GLY—ALA—GLY—
THR—PRO—NH$_2$ Salmon Calcinonin:
H—CYS—SER—ASN—LEU—SER—THR—CYS—VAL—LEU—GLY—
LYS—LEU—SER—GLN—GLU—LEU—HIS—LYS—LEU—GLN—
THR—TYR—PRO—ARG—THR—ASN—THR—GLY—SER—GLY—
THR—PRO—NH$_2$ Human Calcitonin:
H—CYS—GLY—ASN—LEU—SER—THR—CYS—MET—LEU—GLY—
THR—TYR—THR—GLN—ASP—PHE—ASN—LYS—PHE—HIS—
TYR—PHE—PRO—GLN—THR—ALA—ILE—GLY—VAL—GLY—
ALA—PRO—NH$_2$

Typical Peptides Containing Cysteine Ring Structure
—continued

Porcine Calcitonin:

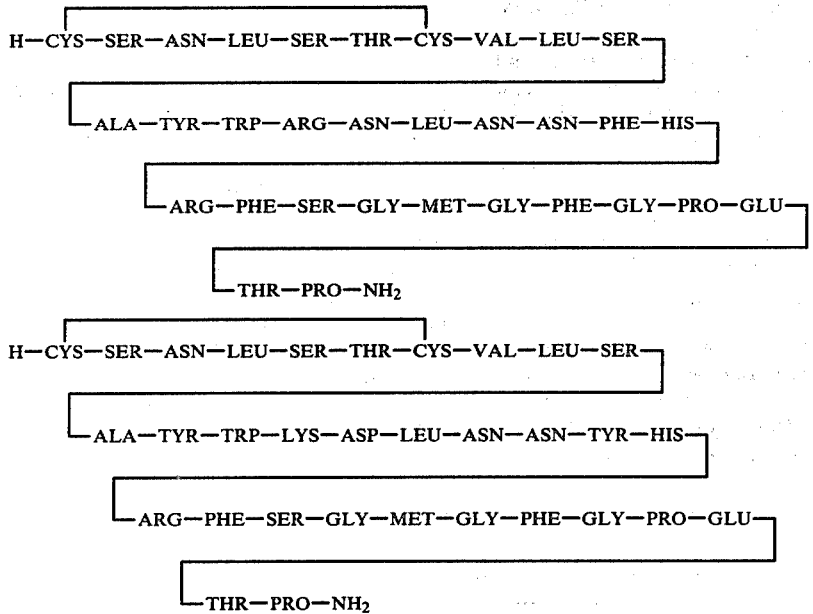

Bovine Calcitonin:

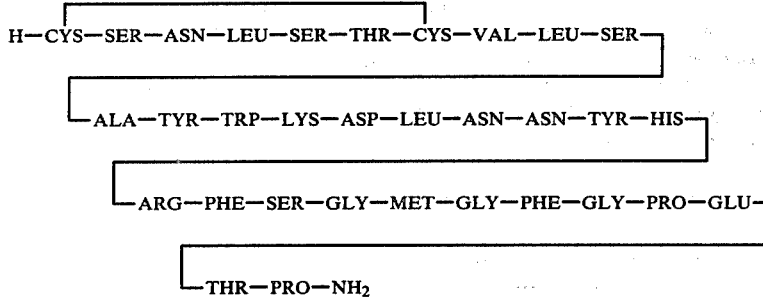

In prior attempts by others to prepare synthetically a peptide such as those referred to in Table I, the only method available for producing a closed disulfide ring structure was to attempt to form the intermediate peptide having the desired amino acid chain and then subject this peptide to an oxidative process using oxidizing agents, to form the disulfide bond between the two cysteine residues. Such oxidative methods have been described in the literature (Katsoyannis, P.G., The Chemistry of Polypeptides, Plenum Press, 1974, pages 60–85). A main disadvantage of these processes is the exposure of the highly labile peptide molecule to oxidizing agents. This treatment can cause inactivation of the peptide resulting in a lower yield of biologically active products.

The art has long needed satisfactory processes for the formation of the disulfide bond between the cysteine moieties of a peptide which do not require the use of oxidizing agents. Accordingly, we have set ourselves to the discovery of practical and efficient methods for the formation of a cyclic disulfide bond between the cysteine moieties of a peptide.

In our co-pending patent applcations Ser. No. 505,344, filed Sept. 12, 1974 and Ser. No. 631,408, filed Nov. 12, 1975, we have discovered methods for forming disulfide bonds between the cysteine moities in a peptide.

SUMMARY

We have now discovered a new method for forming such disulfide bonds in peptides. This new process also avoids the use of oxidative conditions, and involves the use of thiol protective groups for the cysteine residues between which it is desired to form disulfide bonds. These protective groups are linked to the cysteine residues by acid stable disulfide bonds. The procedure then involves only a rearrangement of the external disulfide bonds to form the desired disulfide bond between two of the cysteine residues in the peptide. The by-product in this reaction is a disulfide compound made up by utilizing these two protective groups. The total process thus produces the desired disulfide peptide by a simple mild rearrangement procedure that does not utilize the use of oxidizing reagents or conditions. The process is particularly advantageous in the synthesis of labile biologically active peptides because the disulfide bond formation is performed under conditions which avoid oxidation and do not otherwise disturb the peptide structure.

DESCRIPTION OF INVENTION

We may start with the preparation of an intermediate peptide and build the amino acid chain of the oxytocin, calcitonin or any other such peptide containing two cysteine residues. The amino acid chain may be assembled by application of classical synthesis techniques or the new solid phase techniques (see our U.S. Pat. No. 4,033,940).

We prefer to use the solid phase type of synthesis. In this synthesis the amino acids are added one at a time to the resin until the total peptide sequence has been built up on the resin. The functional groups of the amino acids are protected by blocking groups. The α-amino group of the amino acids is protected by a tertiary butyloxycarbonyl group we designate as BOC. The hydroxyl functions of serine and theonine are protected by a benzyl or benzyl derivative group such as 4-methoxybenzyl, 4-methylbenzyl, 3,4-dimethylbenzyl, 4-chlorobenzyl, 2,6-dichlorobenzyl, 4-nitrobenzyl, benzhydryl, or an equivalent thereof. We use the term BZ to represent benzyl or benzyl derivative groups. The hydroxyl function of tyrosine may be unprotected, may be protected by a benzyl or benzyl derivative group as described above, as a BZ group, or may be protected by a benzyloxycarbonyl or a benzyloxycarbonyl derivative such as 2-chlorobenzyloxycarbonyl or a 2-bromobenzyloxycarbonyl group or equivalent thereof. We use the term W to represent either no protective group, a BZ group, a benzyloxycarbonyl group or a benzyloxycarbonyl derivative group. The guanidino function of arginine may be protected by a nitro group, a tosyl group or an equivalent thereof. We use the character T to represent either a nitro group or a tosyl group. The ε-amino function or lysine may be protected by a benzyloxycarbonyl group or a benzyloxycarbonyl derivative such as 2-chlorobenzyloxycarbonyl, 2-bromobenzyloxycarbonyl, 3,4-dimethylbenzyloxycarbonyl or the equivalent thereof. We use the character V to represent a benzyloxycarbonyl group or a benzyloxycarbonyl derivative group. The protective groups used on the imidazole nitrogen of histidine are the benzyloxycarbonyl group and benzyloxycarbonyl derivatives such as described above for lysine and are designated V. The ω-carboxylic acid groups of glutamic and aspartic acid are protected by a benzyl or benzyl derivative group such as described for the protection of the hydroxyl function of serine and threonine. These protective groups are representated by the character BZ. The acid stable protecting group for the thiol function of cysteine is designated as P. The character P represents an n-alkylthiol group where the alkyl group is preferably from 1 to 8 carbon atoms, such as methyl, ethyl, propyl, butyl, etc., or it can represent an s-cysteinyl group; however the s-cysteinyl protecting group may only be used as a protecting group on a cysteine residue at the amino terminal end of the peptide.

The disulfide peptides, to which our improved process is applicable, have at least two cysteine residues in the amino acid sequence. The disulfide cyclic peptides are obtained in three steps. In the first step an intermediate peptide is produced with functional groups protected when necessary by acid labile groups except for the thiol groups of cysteine, which are protected by the acid stable s-alkylthio or s-cysteinyl groups. The second step in the process is an acid treatment of the intermediate protected peptide to remove all the acid labile protective groups to obtain the intermediate peptide with its cysteine residue thiol functions protected by external disulfide bonds, by n-alkyl groups, or in the case of an amino terminal cysteine residue, the thiol function may be protected by an s-crysteinyl group. The third step of the process is the formation of the desired disulfide peptide by rearrangement of the external disulfide bonds to form the desired disulfide peptide and a by-product disulfide compound.

The three steps of the process are schematically shown as follows:

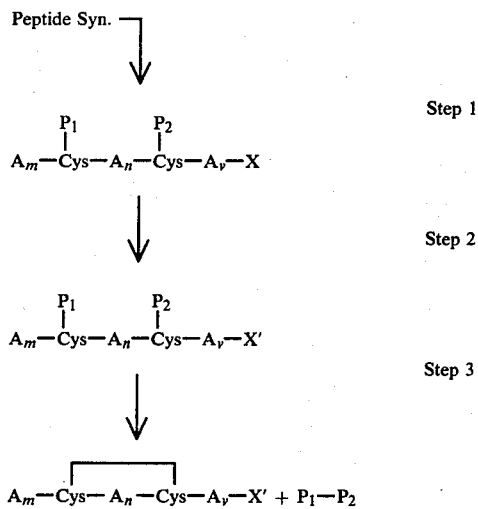

where
A is a peptide chain containing m, n or v amino acid residues with or without blocking groups,
m, n, and v are zero or an integer to give a desired peptide sequence,
X is $NH_2$, OH, a carboxylic acid blocking group or a solid phase resin support,
X' is $NH_2$ or OH,
$P_1$ is an n-alkylthio group, or if m is equal to zero, $P_1$ may be an s-crysteinyl group, and
$P_2$ is an n-alkylthio group.

According to the solid phase technology, the amino acid is the highest numbered position in the chain of the peptide to be synthesized is coupled to the resin using the protective groups as above referred to followed by removal of the BOC protective group of the α-amino group; then the next amino acid of the next highest position is coupled to the amino acid group last added using appropriate protective groups, etc. until the desired chain of amino acids is completed. Suitable combinations of amino acid groups and protective groups may be obtained and these combinations reacted with the peptide previously formed to add the successive amino acid groups. Such protected amino acids may be obtained commercially from chemical supply houses.

To illustrate the synthesis of amino acid chains occurring in typical peptides to which our process is applicable, we give in Tables II to VII some typical reactants (which contain the amino acid group and protecting groups) for use in the synthesis of typical amino acid chain sequences.

TABLE II

| Position Number | Typical Reactants for Use in the Synthesis of Oxytocin Amino Acid Reactant |
|---|---|
| 9 | BOC-glycine |
| 8 | BOC-L-leucine |
| 7 | BOC-L-proline |
| 6 | BOC-S-methylthio-L-cysteine, BOC-S-ethylthio-L-cysteine, BOC-S-n-propylthio-L-cysteine, or BOC-S-n-butylthio-L-cysteine |
| 5 | BOC-L-aspargine p-nitrophenyl ester |
| 4 | BOC-L-glutamine p-nitrophenol ester |
| 3 | BOC-L-isoluecine |
| 2 | BOC-O-benzyl-L-tyrosine BOC-L-tyrosine, or |

TABLE II-continued

Typical Reactants for Use in the Synthesis of Oxytocin

| Position Number | Amino Acid Reactant |
|---|---|
| 1 | BOC-O-2-bromobenzyloxycarbonyl-L-tyrosine BOC-S-methylthio-L-cysteine, BOC-S-ethylthio-L-cysteine, BOC-S-n-propylthio-L-cysteine, BOC-S-n-butylthio-L-cysteine, or Bis-BOC-L-cystine |

TABLE III

Typical Reactants for Use in the Synthesis of Salmon Calcitonin

| Position Number | Amino Acid Reactant |
|---|---|
| 32 | BOC-L-proline |
| 31 | BOC-O-benzyl-L-threonine |
| 30 | BOC-glycine |
| 29 | BOC-O-benzyl-L-serine |
| 28 | BOC-glycine |
| 27 | BOC-O-benzyl-L-threonine |
| 26 | BOC-L-aspargine p-nitrophenyl ester |
| 25 | BOC-O-benzyl-L-threonine |
| 24 | BOC-ω-nitro-L-arginine or BOC-ω-tosyl-L-arginine |
| 23 | BOC-L-proline |
| 22 | BOC-O-benzyl-L-tyrosine, BOC-L-tyrosine, or BOC-O-2-bromo-benzyloxycarbonyl-L-tyrosine |
| 21 | BOC-O-benzyl-L-threonine |
| 20 | BOC-L-glutamine p-nitrophenyl ester |
| 19 | BOC-L-leucine |
| 18 | BOC-ε-CBZ-L-lysine or BOC-ε-2-chlorobenzyloxycarbonyl-L-lysine |
| 17 | BOC-N(im)-CBZ-L-histidine |
| 16 | BOC-L-leucine |
| 15 | BOC-L-glutamic acid γ-benzyl ester |
| 14 | BOC-L-glutamine p-nitrophenyl ester |
| 13 | BOC-L-benzyl-L-serine |
| 12 | BOC-L-leucine |
| 11 | BOC-ε-CBZ-L-lysine or BOC-ε-2-chlorobenzyloxycarbonyl-L-lysine |
| 10 | BOC-glycine |
| 9 | BOC-L-leucine |
| 8 | BOC-L-valine |
| 7 | BOC-S-methylthio-L-cysteine, BOC-S-ethylthio-L-cysteine, BOC-S-n-propylthio-L-cysteine, or BOC-S-n-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | BOC-S-methylthio-L-cysteine, BOC-S-ethylthio-L-cysteine, BOC-S-n-propylthio-L-cysteine, BOC-S-n-butylthio-L-cysteine, or Bis-BOC-L-cystine |

TABLE IV

Typical Reactants For Use In The Synthesis of Human Calcitonin

| Position Number | Amino Acid Reactant |
|---|---|
| 32 | BOC-L-proline |
| 31 | BOC-L-alanine |
| 30 | BOC-glycine |
| 29 | BOC-L-valine |
| 28 | BOC-glycine |
| 27 | BOC-L-isoleucine |
| 26 | BOC-L-alanine |
| 25 | BOC-O-benzyl-L-threonine |
| 24 | BOC-L-glutamine-p-nitrophenyl ester |
| 23 | BOC-L-proline |

TABLE IV-continued

Typical Reactants For Use In The Synthesis of Human Calcitonin

| Position Number | Amino Acid Reactant |
|---|---|
| 22 | BOC-L-phenylalanine |
| 21 | BOC-O-benzyl-L-threonine |
| 20 | BOC-N(im)-CBZ-L-histidine |
| 19 | BOC-L-phenylalanine |
| 18 | BOC-ε-CBZ-L-lysine or BOC-ε-2-chlorobenzyloxycarbonyl-L-lysine |
| 17 | BOC-L-asparagine p-nitrophenyl ester |
| 16 | BOC-L-phenylalanine |
| 15 | BOC-L-aspartic acid γ-benzyl ester |
| 14 | BOC-L-glutamine p-nitrophenyl ester |
| 13 | BOC-O-benzyl-L-threonine |
| 12 | BOC-O-benzyl-L-tyrosine, BOC-L-tyrosine, or BOC-O-bromo-benzyloxycarbonyl-L-tyrosine |
| 11 | BOC-O-benzyl-L-threonine |
| 10 | BOC-glycine |
| 9 | BOC-L-leucine |
| 8 | BOC-L-methionine |
| 7 | BOC-S-methylthio-L-cysteine, BOC-S-ethylthio-L-cysteine, BOC-S-n-propylthio-L-cysteine, or BOC-S-n-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-glycine |
| 1 | BOC-S-methylthio-L-cysteine, BOC-S-ethylthio-L-cysteine, BOC-S-n-propylthio-L-cysteine, BOC-S-n-butylthio-L-cysteine, or Bis-BOC-L-cystine |

TABLE V

Typical Reactants for Use In The Synthesis of Vasopressin

| Position Number | Amino Acid Reactant |
|---|---|
| 9 | BOC-glycine |
| 8 | BOC-ω-tosyl-L-arginine or BOC-ω-nitro-L-arginine |
| 7 | BOC-L-proline |
| 6 | BOC-S-methylthio-L-cysteine, BOC-S-ethylthio-L-cysteine, BOC-S-n-propylthio-L-cysteine, or BOC-S-n-butylthio-L-cysteine |
| 5 | BOC-L-asparagine p-nitrophenyl ester |
| 4 | BOC-L-glutamine p-nitrophenyl ester |
| 3 | BOC-L-phenylalanine |
| 2 | BOC-O-benzyl-L-tyrosine, BOC-L-tyrosine, or BOC-O-2-bromobenzyloxycarbonyl-L-tyrosine |
| 1 | BOC-S-methylthio-L-cysteine, BOC-S-n-propylthio-L-cysteine, BOC-S-n-butylthio-L-cysteine, or Bis-BOC-L-cystine |

TABLE VI

Typical Reactants For Use In The Synthesis of Porcine Calcitonin

| Position Number | Amino Acid Reactant |
|---|---|
| 32 | BOC-L-proline |
| 31 | BOC-O-benzyl-L-threonine |
| 30 | BOC-L-glutamic acid γ-benzyl ester |
| 29 | BOC-L-proline |
| 28 | BOC-glycine |
| 27 | BOC-L-phenylalanine |
| 26 | BOC-glycine |
| 25 | BOC-L-methionine |
| 24 | BOC-glycine |
| 23 | BOC-O-benzyl-L-serine |
| 22 | BOC-L-phenylalanine |

TABLE VI-continued

| Position Number | Typical Reactants For Use In The Synthesis of Porcine Calcitonin Amino Acid Reactant |
|---|---|
| 21 | BOC-ω-tosyl-L-arginine or BOC-ω-nitro-L-arginine |
| 20 | BOC-N(im)-CBZ-L-histidine |
| 19 | BOC-L-phenylalanine |
| 18 | BOC-L-asparagine p-nitrophenyl ester |
| 17 | BOC-L-asparagine p-nitrophenyl ester |
| 16 | BOC-L-leucine |
| 15 | BOC-L-asparagine p-nitrophenyl ester |
| 14 | BOC-ω-tosyl-L-arginine or BOC-ω-nitro-L-arginine |
| 13 | BOC-L-tyrptophan |
| 12 | BOC-O-benzyl-L-tyrosine, BOC-L-tyrosine, or BOC-2-bromobenzyloxycarbonyl-L-tyrosine |
| 11 | BOC-L-alanine |
| 10 | BOC-O-benzyl-L-serine |
| 9 | BOC-L-leucine |
| 8 | BOC-L-valine |
| 7 | BOC-S-methylthio-L-cysteine, BOC-S-ethylthio-L-cysteine, BOC-S-n-propylthio-L-cysteine, or BOC-S-n-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | BOC-S-methylthio-L-cysteine, BOC-S-ethylthio-L-cysteine, BOC-S-n-propylthio-L-cysteine, BOC-S-n-butylthio-L-cysteine, or Bis-BOC-L-cystine |

TABLE VII

| Position Number | Typical Reactants For Use In The Synthesis of Bovine Calcitonin Amino Acid Reactant |
|---|---|
| 32 | BOC-L-proline |
| 31 | BOC-O-benzyl-L-threonine |
| 30 | BOC-L-glutamic acid γ-benzyl ester |
| 29 | BOC-L-proline |
| 28 | BOC-glycine |
| 27 | BOC-L-phenylalanine |
| 26 | BOC-glycine |
| 25 | BOC-L-methionine |
| 24 | BOC-glycine |
| 23 | BOC-O-benzyl-L-serine |
| 22 | BOC-L-phenylalanine |
| 21 | BOC-ω-tosyl-L-arginine or BOC-ω-nitro-L-arginine |
| 20 | BOC-N(im)-CBZ-L-histidine |
| 19 | BOC-O-benzyl-L-tyrosine, BOC-L-tyrosine, or BOC-O-2-bromobenzyloxycarbonyl-L-tyrosine |
| 18 | BOC-L-asparagine p-nitrophenyl ester |
| 17 | BOC-L-asparagine p-nitrophenyl ester |
| 16 | BOC-L-leucine |
| 15 | BOC-L-aspartic acid γ-benzyl ester |
| 14 | BOC-ω-CBZ-L-lysine or BOC-ε-2-chlorobenzyloxycarbonyl-L-lysine |
| 13 | BOC-L-tryptophan |
| 13 | BOC-O-benzyl-L-tyrosine, BOC-L-tyrosine, or BOC-O-2-bromobenzyloxycarbonyl-L-tyrosine |
| 11 | BOC-L-alanine |
| 10 | BOC-O-benzyl-L-serine |
| 9 | BOC-L-leucine |
| 8 | BOC-L-valine |
| 7 | BOC-S-methylthio-L-cysteine, BOC-S-ethylthio-L-cysteine, BOC-S-n-propylthio-L-cysteine, or BOC-S-n-butylthio-L-cysteine |
| 6 | BOC-O-benzyl-L-threonine |
| 5 | BOC-O-benzyl-L-serine |

TABLE VII-continued

| Position Number | Typical Reactants For Use In The Synthesis of Bovine Calcitonin Amino Acid Reactant |
|---|---|
| 4 | BOC-L-leucine |
| 3 | BOC-L-asparagine p-nitrophenyl ester |
| 2 | BOC-O-benzyl-L-serine |
| 1 | BOC-S-methylthio-L-cysteine, BOC-S-ethylthio-L-cysteine, BOC-S-n-propylthio-L-cysteine, BOC-S-n-butylthio-L-cysteine, or Bis-BOC-L-cystine |

TABLE VIII

| Position Number | Typical Reactants For Use In The Synthesis of Eel Calcitonin Amino Acid Reactant |
|---|---|
| 32 | BOC-L-proline |
| 31 | BOC-O-benzyl-L-threonine |
| 30 | BOC-glycine |
| 29 | BOC-L-alanine |
| 28 | BOC-glycine |
| 27 | BOC-L-valine |
| 26 | BOC-L-aspartic acid γ-benzyl ester |
| 25 | BOC-O-benzyl-L-threonine |
| 24 | BOC-ω-nitro-L-arginine or BOC-ω-tosyl-L-arginine |
| 23 | BOC-L-proline |
| 22 | BOC-O-benzyl-L-tyrosine, BOC-L-tyrosine, or BOC-O-2-bromo-benzyloxycarbonyl-L-tyrosine |
| 21 | BOC-O-benzyl-L-threonine |
| 20 | BOC-L-glutamine p-nitrophenyl ester |
| 19 | BOC-L-leucine |
| 18 | BOC-ε-CBZ-L-lysine or BOC-ω-2-chlorobenzyloxycarbonyl-L-lysine |
| 17 | BOC-N(im)-CBZ-L-histidine |
| 16 | BOC-L-leucine |
| 15 | BOC-L-glutamic acid γ-benzyl ester |
| 14 | BOC-L-glutamine p-nitrophenyl ester |
| 13 | BOC-L-benzyl-L-serine |
| 12 | BOC-L-leucine |
| 11 | BOC-ε-CBZ-L-lysine or BOC-ε-2-chlorobenzyloxycarbonyl-L-lysine |
| 10 | BOC-glycine |
| 9 | BOC-L-leucine |
| 8 | BOC-L-valine |
| 7 | BOC-S-methylthio-L-cysteine, BOC-S-ethylthio-L-cysteine, BOC-S-n-propylthio-L-cysteine, or BOC-S-n-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | BOC-S-methylthio-L-cysteine, BOC-S-ethylthio-L-cysteine, BOC-S-n-propylthio-L-cysteine, BOC-S-n-butylthio-L-cysteine, or Bis-BOC-cystine |

TABLE IX

| Position Number | Typical Reactants For Use In The Synthesis of Somatostatin Amino Acid Reactant |
|---|---|
| 14 | BOC-S-methylthio-L-cysteine, BOC-S-ethylthio-L-cysteine, BOC-S-n-propylthio-L-cysteine, or BOC-S-n-butylthio-L-cysteine |
| 13 | BOC-O-benzyl-L-serine |
| 12 | BOC-O-benzyl-L-threonine |
| 11 | BOC-L-phenylalanine |
| 10 | BOC-O-benzyl-L-threonine |
| 9 | BOC-ε-CBZ-L-lysine or |

| Position Number | Typical Reactants For Use In The Synthesis of Somatostatin Amino Acid Reactant |
|---|---|
|  | BOC-ε-2-chlorobenzyloxycarbonyl-L-lysine |
| 8 | BOC-L-tryptophan |
| 7 | BOC-L-phenylalanine |
| 6 | BOC-L-phenylalanine |
| 5 | BOC-L-asparagine p-nitrophenyl ester |
| 4 | BOC-ε-CBZ-L-lysine or BOC-ε-2-chlorobenzylcarbonyl-L-lysine |
| 3 | BOC-S-methylthio-L-cysteine, BOC-S-ethylthio-L-cysteine, BOC-S-n-propylthio-L-cysteine, or BOC-S-n-butylthio-L-cysteine |
| 2 | BOC-glycine |
| 1 | BOC-alanine |

The peptides containing at least two cysteine residues in their sequences which we prepare as intermediates in our process or characterized before acid cleavage by their containing the following structure:

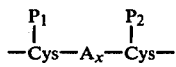

and after acid treatment to cleave the acid labile protective groups, thus obtaining the structure:

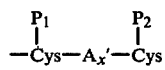

where
A is an amino acid residue with acid labile protecting groups,
A' is an amino acid residue with protecting groups removed,
x is zero or an integer,
$P_1$ is an n-alkylthio group, or if Cys is at the amino terminal may be an S-cysteinyl group, and
$P_2$ is an n-alkyl thio group.

The cleaved peptide thus has protecting groups remaining on the thiol function of its cysteine residues. In the instance where $P_1$ and $P_2$ are each n-alkylthio groups, the cleaved peptide will contain the structure:

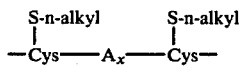

In the instance where the cysteine residue, Cys, is at the amino terminal end of the peptide, $P_1$ may be an S-cysteinyl group, the cleaved peptide group, and the cleaved peptide will contain the structure:

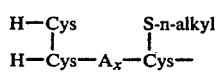

Thus the cleaved peptides contain cysteine residues with their thiol groups protected by participation in external disulfide bonds with various protecting groups. Such peptides can be converted to the desired cyclic disulfide peptides by a simple rearrangement of the external disulfide bonds to the desired internal disulfide bond and a by-product nonpeptide disulfide compound.

This is illustrated for the two types described as follows:

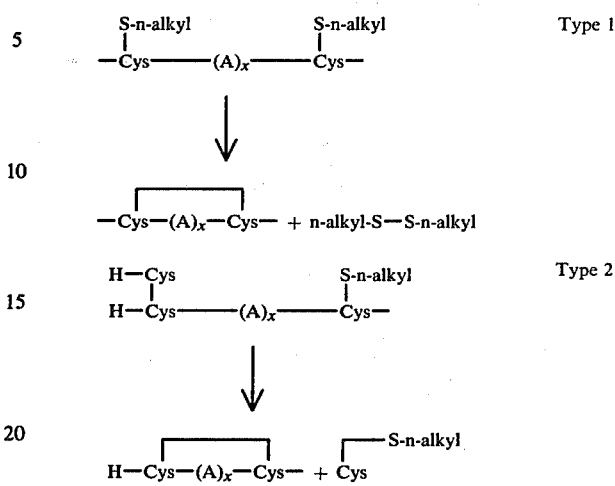

It will be seen that the peptide produced as a result of using the reactants of Table II to Table IX may each be so characterized.

Any peptide which may be characterized as above indicated may be used as an intermediate in our process and subjected to our disulfide rearrangement procedure. Any such peptide containing a structure having two cysteine residues participating in external disulfide bonds with protecting groups may be held in solution (any solution in which it is soluble), with aqeuous or alcoholic solutions preferred, at a preferred pH of from about 5 to 10 until the external disulfide bonds undergo spontaneous rearrangement to the desired internal disulfide peptide with the displacement of a non-peptide disulfide by-product.

The rate of the rearrangement reaction is facilitated by the presence (in amounts of 0.01 molar equivalents per mole of peptide) of a free thiol compound, such as aliphatic or aromatic thiols, the amino acid cysteine or thioglycolic acid or its derivatives. The rate of rearrangement is also facilitated by adjusting the pH of the solution to from 5.0 to 8.5, preferably from 6.0 to 8.5, and better at about 7.5, as by the addition of amonium or alkali hydroxides to the solution. A pH below 6.0 may be used, but the rearrangement proceeds more slowly than is desirable, and a pH up to about 10.0 or 10.5 can be used, but when a pH higher than about 9.0 is used, there is some danger of loss in yield.

Further, we prefer to agitate the solution during the period of the rearrangement reaction which may take from 1 to 48 hours, but is usually complete in 24 hours or less. The reaction is facilitated by stirring or other form of agitation. This treatment may be continued for still longer periods of time without harm to the product.

Also, we take care to avoid the presence of oxygen or other oxidizing substances, and keep the solution substantially free of oxygen. We prefer to place the solution containing the peptide under a stream of inert gas such as nitrogen.

If the procedure has been carefully carried out according to the procedures and precautions outlined above, the disulfide bond rearrangement produces no other changes in the peptide other than the formation of the desired disulfide bond between the two cysteine residues of the peptide and to displace a non-peptide disulfide molecule.

The peptide solution obtained by our disulfide rearrangement procedure as above set forth may be purified by procedures known to this art. The solution may be subjected to a combination of gel-filtration procedures and ion-exchange chromatography methods. The final purified product may be obtained from solution by freeze-drying. The resulting peptide will be found to be chemically and biologically equivalent to such peptide which has been obtained from natural sources.

When position No. 7 is reached, a cysteine derivative containing an acid stable S-N-alkylthio protecting group is used; and when position No. 1 is reached, the acid stable S-N-alkylthio protecting group, or an S-cysteinyl group, may be used. If the latter group is chosen the cysteine derivative used in the synthesis becomes Bis-BOC-L-cystine as indicated in Table III.

The formuli of the peptides resulting from solid-phase peptide synthesis using the amino acid derivative described in Table III, and before acid cleavage, may be written:

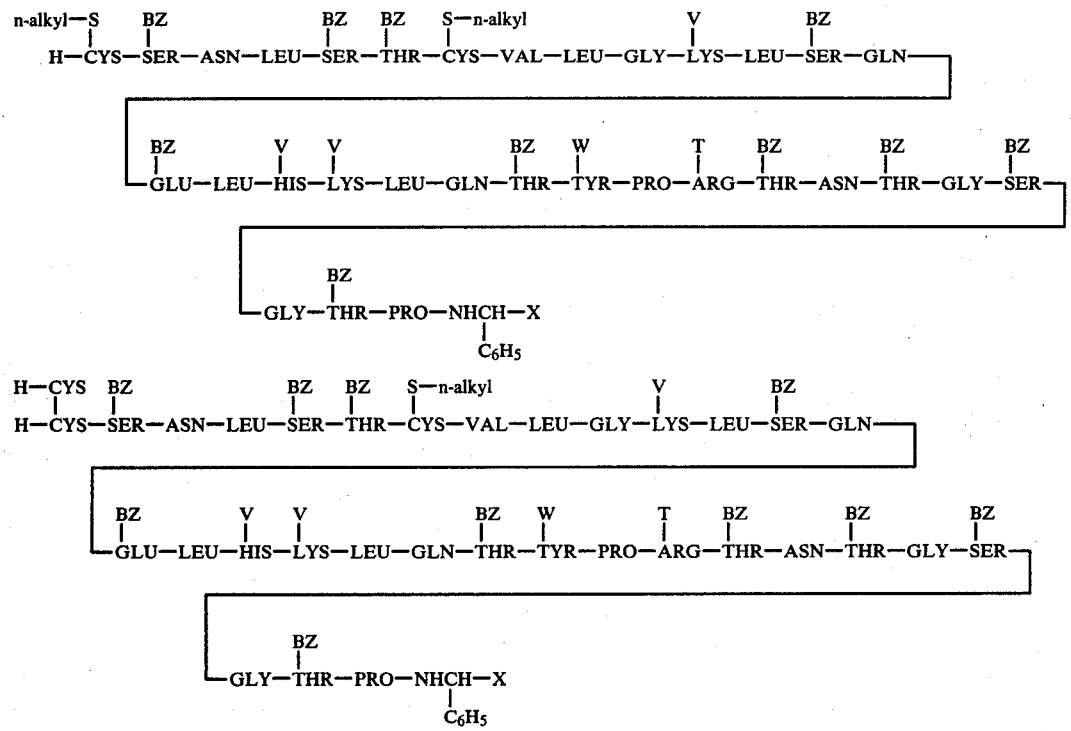

One application of our improved process is in the synthesis of salmon calcitonin. As set forth in Example I, proline may be coupled to the resin using the reactant BOC-L-proline at position 32, then threonine maybe coupled using the reactant BOC-O-benzyl-L-threonine at position No. 31, the coupling being continued using in sequence the reactants set forth in Table III herein.

The formulas of these peptides obtained upon anhydrous halogen acid cleavage become:

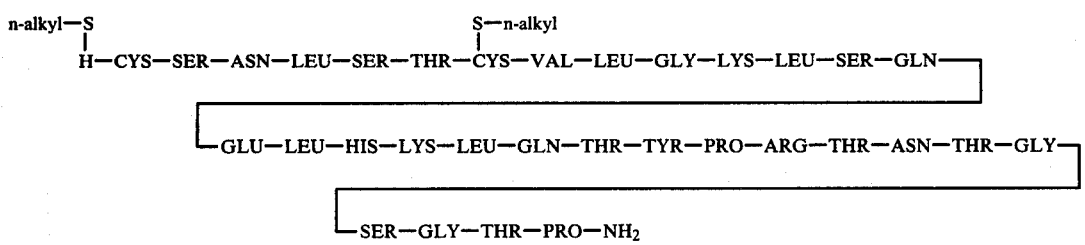

which is precursor of salmon calcitonin.

After subjecting this peptide to our improved cyclizing method as herewith described, the peptide becomes:

```
   ┌─────────────────────────────────────────────────────────────┐
H—CYS SER ASN LEU SER THR CYS VAL LEU GLY LYS LEU SER GLN—┐
                                                               │
   ┌───────────────────────────────────────────────────────────┘
   └GLU LEU HIS LYS LEU GLN THR TYR PRO ARG THR ASN THR GLY—┐
                                                            │
   ┌────────────────────────────────────────────────────────┘
   └SER GLY THR PRO—NH₂
``` which is salmon calcitonin.

A specific example of the synthesis of salmon calcitonin using our improved process is given in Example I.

EXAMPLE I

Resin Activation

The BHA resin (5 g) with an amine titer of 0.61 meq/g was placed in the reactor vessel of a peptide synthesizer marked by Schwarz-Mann, Inc. of Orangeburg, N.Y. The resin was treated with 25 ml of the following solvents filtering after each treatment.

Methylene Chloride—2 minutes
Chloroform—2 minutes two times each
10% triethylamine in chloroform—5 minutes two times each
Chloform—2 minutes
Methylene Chloride—2 minutes three times each

CYCLE 32

Coupling: The BHA resin, 25 ml of methylene chloride and 1.29 g (0.006 moles) or BOC-L-proline was stirred for 10 minutes 6.0 ml of a methylene chloride solution of dicyclohexylcarbodiimide (1 milliequivalent of DCCI per 1 ml of solution) was added to the reactor and the mixture agitated for 6 hours. The reaction mixture was removed from the reactor by filtration and the BOC-prolyl BHA resin subjected to the following successive 2 minute, 25 ml washes, removing the wash by filration each time:

Methylene chloride—two times
Methyl alcohol—two times
Methylene chloride—three times Acetylation: The resin was then agitated with a mixture of 1.5 ml of triethylamine (TEA), 1 ml of acetic anhydride and 25 ml of chloroform for 2 hours. The reaction mixture was removed by filtration and the resin subjected to the following 2 minute, 25 ml washes:

Chloroform—two times
Methyl alcohol—two times
Methylene chloride—three times

Deprotection: The BOC-protected resin was agitated for 5 minutes with a mixture of 15 ml of trifluoroacetic acid (TFA) and 15 ml of methylene chloride. This mixture was removed by filtration and the resin was agitated with a second mixture of 15 ml of TFA and 15 ml of methylene chloride for 30 minutes. The reaction mixture was removed by filtration and the resin subjected to the following 25 ml washes:

Methylene chloride—two times two minutes each
Methyl alcohol—two times two minutes each
Chloroform—two times two minutes each 10% TEA in chloroform—two times ten minutes each
Chloroform—two times two minutes each
Methylene chloride—two times two minutes each The L-proline BHA resin was titrated to establish the amine or proline titer. This value was 0.55 milliequivalents of amine or proline per gram of resin.

CYCLE 31

Coupling: The L-prolyl resin, 25 ml of methylene chloride and 1.7 g (0.0055 mole) of BOC-O-benzyl-L-threonine were agitated for 10 minutes. Then 5.5 ml of a methylene chloride solution of dicyclohexylcarbodiimide (1 milliequivalent of DCCI per 1 ml of solution or a total of 0.0055 mole of DCCI) was added to the reactor and the mixture agitated for 2 hours. The reaction mixture was removed from the reactor and the resin was subjected to the following successive 2 minutes, 25 ml washes, removing the wash by filtration each time.

Methylene chloride—two times
Methyl alcohol—two times
Methylene chloride—three times A ninhydrin test was negative.

Deprotection: The deprotection procedure described in Cycle 32 was repeated for this cycle.

CYCLES 30 through 27

The coupling and deprtoection procedures used in these cycles were the same as in Cycle 31 except that the following amino acid derivatives were used in place of the threonine derivative:

Cycle 30—0.97 g. (0.0055 mole) of BOC-glycine
Cycle 29—1.62 g. (0.0055 mole) of BOC-O-Benzyl-L-serine
Cycle ∞—The material used was the same as Cycle 30.
Cycle 27—The material used was the same as Cycle 31.

CYCLE 26

Coupling: The peptide resin obtained from Cycle 27 was washed twice with 25 ml portions of dimethylformamide (DMF). The resin was then agitated for 24 hours with a solution of 2.9 g (0.008 mole) of BOC-L-asparagine p-nitrophenyl ester in 35 ml of DMF. The reaction mixture was filtered and the resin peptide subjected to two minute washes with two successive 25 ml portions of the following solvents: DMF, methylene chloride, methanol, methylene chloride. Each individual solvent was removed by filtration. A ninhydrin test was negative.

Deprotection: The deprotection procedure used in Cycle 32 was repeated.

CYCLE 25

Coupling and deprotection procedures were the same as Cycle 31 using the same materials and amounts.

CYCLE 24

Coupling: The resin peptide obtained from Cycle 25 was washed with two successive 25 ml portions of DMF. The resin peptide was then agitated for 10 minutes with a mixture of 3.43 g (01008 mole) of BOC-N-tosyl-L-arginine and 25 ml of DMF. Then 8 ml of DCCI in methylene chloride (equivalent to 0.008 mole of DCCI) was added and the mixture agitated for 6 hours. The reaction mixture was removed by filtration. The resin peptide was subjected to two minute washes with two successive 25 ml portions of the following solvents: DMF, methylene chloride, methyl alcohol, methylene chloride. The ninhydrin test was negative.

Deprotection: Repeat deprotection procedures used in Cycle 32.

CYCLE 23

Coupling: The peptide resin obtained from Cycle 24 was agitated for 10 minutes with 1.77 g (0.008 mole) of BOC-L-proline and 25 ml of methylene chloride. 8 ml of DCCI in methylene chloride (equivalent to 0.008 mole of DCCI) was added and the mixture agitated for 6 hours. The reaction mixture was removed by filtration and the resin peptide subjected to two minute washes with two successive 25 ml portions of the following solvents: methylene chloride, methyl alcohol, methylene chloride. Each individual solvent was removed by filtration. The ninhydrin test was negative.

Deprotection: The deprotection procedure used in Cycle 32 was repeated.

CYCLES 22 and 21

The coupling and deprotection procedures used in these cycles were the same as in Cycle 24 except that in the coupling reaction the following amino acid derivatives were used in place of BOC-L-proline.

Cycle22—2.97 g (0.008 mole) of BOC-O-benzyl-L-tyrosine

Cycle 21—2.74 g (0.008 mole) of BOC-O-benzyl-L-threonine

CYCLE 20

This procedure is the same as Cycle 26 except that 3.0 g (0.008 mole) of BOC-L-glutamine p-nitrophenyl ester is used in place of the asparagine derivative.

CYCLES 19 through 15

The procedure is the same as used in Cycle 31 except that the following amino acid derivatives were used in place of the threonine derivative:

Cycle 19—1.37 g (0.0055 mole) of BOC-L-leucine

Cycle 18—2.09 g (0.0055 mole) of BOC-ε-carbobenzyloxy-L-lysine

Cycle 17—2.58 g (0.0055 mole) of BOC-N(im) carbobenzyloxy-L-lysine

Cycle 16—See Cycle 19

Cycle 15—1.85 g (0.0055 mole) of BOC-L-glutamic acid γ-benzyl ester

CYCLE 14

Same as Cycle 20.

CYCLE 13

The procedure used was the same as used in Cycle 23 except that in the coupling reaction 2.36 g (0.008 mole) of BOC-O-benzyl-L-serine was used in place of the proline derivative.

CYCLES 12 through 9

The prodecures used were the same as used in Cycle 31 except in the coupling reactions the following amino acid derivatives were used in place of the threonine derivative.

Cycle 12—Same material as used in Cycle 19

Cycle 11—The material used was the same as in Cycle 18

Cycle 10—Same material as used in Cycle 30

Cycle 9—Same material as used in Cycle 19

CYCLE 8

Coupling: The resin peptide from Cycle 9 was agitated for 10 minutes with 1.79 g (0.008 mole) of BOC-L-valine and 25 ml of methylene chloride. Then 8 ml of DCCI in methylene chloride (equivalent to 0.008 mole of DCCI) was added and the mixture agitated for 16 hours. The reaction mixture was removed by filtration. The resin peptide was subjected to two minute washes with two successive 25 ml portions of the following solvents: methylene chloride, methyl alcohol, methylene chloride. Each individual was removed by filtration.

Deprotection: See Cycle 22.

CYCLE 7

The procedure was the same as used in Cycle 31 except that in the coupling reaction 1.55 g (0.0055 mole) of BOC-S-ethylthio-L-cysteine was used in place of the threonine derivative.

CYCLE 6

The materials and procedures used were the same as Cycle 31.

CYCLE 5

The materials and procedures used were the same as Cycle 29.

CYCLE 4

The materials and procedures used were the same as Cycle 19.

CYCLE 3

The materials and procedures used were the same as Cycle 26.

CYCLE 2

The materials and procedures used were the same as Cycle 29.

CYCLE 1

The resin peptide obtained from Cycle 2 was washed with two successive 20 ml portions of DMF. The resin peptide was then agitated for 10 minutes with a mixture of 2.4 g (0.0055 mole) of bis-BOC-L-cystine and 20 ml of DMF. Then 11.0 ml of methylene chloride solution of dicyclohexylcarbodiimide (1 meq of DCCI per ml of solution or a total of 0.011 mole of DCCI) was added to the reactor and the mixture agitated for 2 hours. The reaction mixture was removed from the reactor and the resin peptide was subjected to the following successive 2 minute, 20 ml washes, removing the wash by filtration each time.

DMF—two times

Methylene chloride—two times

Methyl alcohol—two times

A ninhydrin test was negative.

Deprotection: Repeat the deprotection procedure used in Cycle 31.

After completion of Cycle 1 the resin peptide was washed with two successive 25 ml portions of n-hexane. The peptide material was removed from the reactor and dried in an electric vacuum oven at 40° C. and 0.1 mm of Hg for 24 hours.

Cleavage with Hydrogen Fluoride

The dried resin peptide (16 g) and 16 ml of anisole were placed in a Teflon reaction vessel. The vessel equipped with a Teflon-coated magnetic stirrer was placed in a dry ice-acetone bath and 100 ml of hydrogen fluoride gas was condensed into the vessel. This mixture was stirred at 0° C. in an ice bath for 1 hour. The hydrogen fluoride was removed by evaporation at reduced pressure. The residue was triturated with six 100 ml portions of ethyl acetate. The peptide was extracted from the resin beads with 800 ml of 0.1 molar aqueous acetic solution.

Cyclization of Peptide to Salmon Calcitonin

The aqueous acetic acid extract obtained from hydrogen fluoride cleavage was diluted to 1.5 liters by addition of 700 ml of distilled water. The pH of the solution was adjusted to 7.5 by the addition of concentrated ammonium hydroxide. The solution was stirred in a closed vessel under a stream of nitrogen for 12 hours. The pH of the reaction mixture was adjusted to 5.0 by addition of glacial acetic acid.

Purification of the Crude Salmon Calcitonin

The 1.5 liters of solution from the above synthesis at pH 5.0 was concentrated using a SP-Sephadex C-25 ion-exchange column. The 75 ml concentrate removed from the column with 0.5 molar sodium chloride solution was desalted and purified by passing through a Sephadex G-25 (fine) gel-filtration column and eluting with 0.03 molar aqueous acetic acid solution. The salmon calcitonin fraction from this column was adjusted to pH 6.0 by addition of ammonium hydroxide solution. This solution was further purified by ion-exchange chromatography using a Whatman CM52 column eluted with ammonium acetate buffer. The salmon calcitonin fraction from this column was adjusted to pH 5.0 by addition of glacial acetic acid. This solution was concentrated using a SP-Sephadex C-25 ion-exchange column. The 30 ml concentrate removed from the column with 0.5 molar sodium chloride solution was desalted with a Sephadex G-25 (fine) gel-filtration column. The purified salmon calcitonin fraction was collected and freeze-dried. The product was obtained as a fluffy white solid. This material was found to be biologically and chemically equivalent to the product reported in literature (Guttman, S., et., Helv. Chim. Acta 52, 1789–1795 [1969]).

The preparation of the compounds as heretofore described or as set forth in Example I may be varied in many respects, but when variations in more than one factor are made it is difficult to evaluate any one of the changed factors. For this reason, we set up a series of tests in which only one factor is varied and the results compared.

Another application of our improved process is in the synthesis of oxytocin. Oxytocin includes nine amino acids, and the amino acid chain for oxytocin may be built beginning with glycine at position 9. The glycine may be coupled to the BHA resin using the reactant BOC-glycine; then leucine may be coupled using the reactant BOC-L-leucine, and then following through using cycles of coupling and deprotection according to the solid phase technique, using in sequence the specified amino acid groups and protective groups as set forth in Table III.

When position No. 6 is reached, an S-n-alkylthio protected cysteine derivative is used and when position No. 1 is reached, an S-n-alkylthio protected cysteine derivative can be used or bis-BOC-L-cystine, an S-cysteinyl protected cysteine derivative may be used.

The peptides after completion of the amino acid sequence may be written:

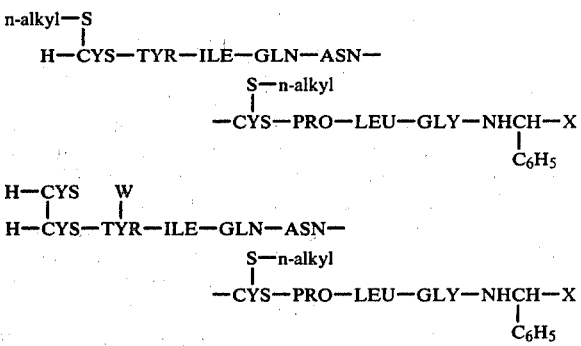

where
X is the polystyrene portion of the resin
W is no protective group, a BZ group, or benzyloxycarbonyl group or a benzyloxycarbonyl derivative group.

After acid treatment to remove the acid labile groups and to remove the peptides from the resin, the peptides become:

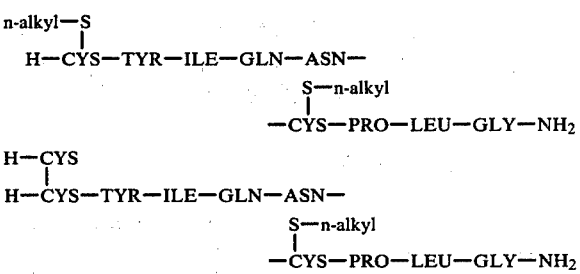

The cleaved peptides, when held in aqueous or alcoholic solvents, preferably at pH 6.0 to 8.5, undergo rearrangement of disulfide bonds to form the internal bond between the cysteine residues at positions No. 1 and No. 6 to yeild the peptide written as follows:

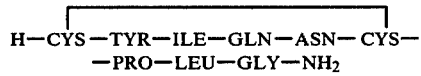

which is oxytocin

A specific example of the synthesis of oxytocin using our improved process is given in the following Example II.

EXAMPLE II

Synthesis of Oxytocin

Resin Activation

The benzhydrylamine (BHA) resin (5 g) with an amine titer of 0.43 meq/g was placed in the reaction vessel of a peptide synthesizer marketed by Schwartz-Mann, Inc. of Orangeburg, New York. The resin was treated with 20 ml of the following solvents filtering after each treatment:

Methylene chloride—two minutes
Chloroform—two minutes two times each 10% triethylamine in chloroform—five minutes two times each
Chloroform—two minutes
Methylene chloride—two minutes three times each Coupling: The BHA resin, 20 ml of methylene chloride and 0.75 g (0.0043 mole) of BOC-glycine were agitated for 10 minutes. 4.3 ml of methylene chloride solution of dicyclohexylcarbodiimide (1 meq of DCCI per 1 ml of solution) was added to the reactor and the mixture agitated for 6 hours. The reaction mixture was removed from the reactor by filtration and the BOC-glycyl BHA resin subjected to the following successive 2 minute, 2 ml washes, removing the wash by filtration each time:

Methylene chloride—two times
Methyl alcohol—two times
Methylene chloride—two times Acetylation: The resin was then agitated with a mixture of 1.6 ml of acetic anhydride, 2.4 ml of triethylamine (TFA) and 20 ml of chloroform for 30 minutes. The reaction mixture was removed by filtration and the resin subjected to the following 2 minute, 20 ml washes:

Chloroform—two times
Methyl alcohol—two times
Methylene chloride—three times

A negative test was found for a ninhydrin assay.

Deprotection: The BOC-protected resin was agitated for 5 minutes with a mixture of 12 ml of trifluoroacetic acid (TFA) and 13 ml of methylene chloride. The mixture was removed by filtration and the resin was agitated with a second mixture of 12 ml of TFA and 12 ml of methylene chloride for 30 minutes. The reaction mixture was removed by filtration and the resin subjected to the following 20 ml washes.

Methylene chloride—2 times two minutes each
Methyl alcohol—2 times two minutes each
Chloroform—2 times two minutes each
10% TEA in chloroform—2 times five and ten minutes
Chloroform—2 times two minutes each
Methylene chlofide—2 times two minutes each The L-glycine BHA resin was titrated (Dorman, L., Tetrahedron Letters, 1969, 2319-21) to establish the amine or glycine titer. This value was 0.384 meq of amine of glycine per gram of resin.

CYCLE 8

Coupling: The L-glycin resin, 20 ml of methylene chloride and 2.95 g (0.0038 mole) of BOC-L-leucine H$_2$O were agitated for 10 minutes. Then 3.8 ml of methylene chloride solution of dicyclohexylcarbodiimide (1 meq of DCCI) was added to the reactor and the mixture agitated for 2 hours. The reaction mixture was removed from the reactor and the resin was subjected to the following successive 2 minute, 20 ml washes, removing the wash by filtration each time:

Methylene chloride—two times
Methyl alcohol—two times
Methylene chloride—two times A ninhydrin test was negative.

Deprotection: The deprotection procedure described in Cycle 9 was repeated for this cycle.

CYCLE 7

The coupling and deprotection procedures used in this cycle were the same as in Cycle 8 except that the following amino acid derivative was used in place of the leucine derivative:

0.82 g (0.0038 mole) of BOC-L-proline

CYCLE 6

The coupling and deprotection procedures used in this cycle were the same as in Cycle 8. The acetylation procedure was performed in this cycle using the same method as in Cycle 9. The following amino acid derivative was used in the coupling procedure:

1.07 g (0.0038 mole) of BOC-S-ethylthio-L-cysteine

CYCLE 5

Coupling: The peptide resin obtained from Cycle 6 was washed twice with 20 ml portions of dimethylformamide (DMF). The resin was then agitated for 24 hours with a solution of 2.01 g (0.0057 mole) of BOC-L-asparagine-p-nitrophenyl ester in 25 ml of DMF. The reaction mixture was filtered and the resin peptide subjected to two minute washes with two successive 20 ml portions of the following solvents: DMF, methylene chloride, methanol, methylene chloride. Individual solvent washes were removed by filtration. A ninhydrin test was negative.

Deprotection: The deprotection procedure used in Cycle 8 was repeated.

CYCLE 4

The coupling procedure used in this cycle was the same as in Cycle 5. The acetylation procedure was performed in this cycle using the same method as in Cycle 9. The deprotection procedure used in this cycle was the same as in Cycle 8. The following amino acid derivative was used:

2.09 g (b 0.0057 mole) of BOC-L-glutamine-p-nitrophenyl ester

CYCLE 3

The coupling procedure used in this cycle was the same as in Cycle 8. The coupling was repeated using a solvent system of DMF 10 ml and methylene chloride 10 ml and the same amounts of amino acid and DCC. The acetylation procedure used in this cycle was the same as in Cycle 9. The deprotection procedure used in this cycle was the same as in Cycle 8. The following amino acid derivative was used for each coupling reaction:

0/88 g (0.0038 mole) of BOC-L-isoleucine

CYCLE 2

Coupling: The resin peptide obtained from Cycle 3 washed with two successive 20 ml portions of DMF. The resin peptide was then agitated for 10 minutes with a mixture of 2.11 g (0.0057 mole) of BOC-O-benzyl-L-tyrosine and 20 ml of DMF. Then 5.7 ml of DCCi in methylene chloride (equivalent to 0.0057 mole of DCCI) was added and the mixture agitated for 16 hours. The reaction mixture was removed by filtration. The resin peptide was subjected to two minute washes with two succesive 20 ml portions of the following solvents: DMF, methylene chloride, methanol, methylene chloride.

The coupling was repeated using half the amounts of the amino acid derivative and DCCI in methylene chloride for an agitation time of 6 hours.

Acetylation: Repeat acetylation procedure used in Cycle 9.

Deprotection: Repeat deprotection procedure used in Cycle 9.

CYCLE 1

The resin peptide obtained from Cycle 2 was washed with two successive 20 ml portions of DMF. The resin peptide was then agitated for 10 minutes with a mixture of 1.7 g (0.0038 mole) of bis-DOC-L-cystine and 20 ml DMF. Then 7.6 ml of methylene chloride solution of dicyclohexylcarbodiimide (1 meq of DCCI per ml of solution or a total of 0.0076 mole of DCCI) was added to the reactor and the mixture agitated for 2 hours. The reaction mixture was removed from the reactor and the resin peptide was subjected to the following successive 2 minute 20 ml washes, removing the wash by filtration each time:
DMF—two times
Methylene chloride—two times
Methyl alcohol—two times
Methylene chloride—two times
A ninhydrin test was negative.

Deprotection: Repeat the deprotection procedure used in Cycle 9.

The peptide material was removed from the reactor by rinsing with hexane and dried in an electric vacuum oven at 40° C. and 0.1 mm of Hg for 24 hours. The blocked oxytocin peptide resin weighed 6.8 g.

Cleavage with Hydrogen Fluoride

The dried resin peptide (2 g) and 2 ml of anisole were placed in a Teflon reaction vessel. The vessel equipped with a Teflon-coated magnetic stirrer was placed in a dry ice-acetone bath and 15 ml of hydrogen fluoride gas was condensed into the vessel. This mixture was stirred at 0° C. in an ice bath for one hour. The residue was triturated with 4×25 ml portions of ethyl acetate. The peptide was extracted from the resin beads with 2=50 ml portions of glacial acetic acid. The extract was lyophilized to the cleaved peptide.

Cyclization of Peptide to Oxytocin

The crude peptide, 200 mg, was partially dissolved in 50 ml of oxygen-free distilled water with 1 ml of glacial acid added. The pH of the solution was adjusted to 7.5 by the addition of concentrated ammonium hydroxide. This mixture was stirred in a closed vessel under a stream of nitrogen for 24 hours. The reaction mixture was adjusted to pH of 3.2 by addition of glacial acetic acid. It was lyophilized to give a solid residue.

Purification of the Crude Oxytocin

This solid residue was dissolved in 0.5 N acetic acid solution and purified by passing through a Sephadex G-25 (fine) gel-filtration column and eluted with 0.5 N acetic acid. The oxytocin fraction from this column was collected and lyophilized to give a white solid.

This solid was again dissolved in 0.5 N acetic acid solution and purified by passing through the Sephadex G-25 (fine) gel-filtration column and eluted with 0.5 N acetic acid solution. The oxytocin fraction from the column was collected and lyophilized to give a fluffy white solid. This product was assayed for oxytocin activity. The result was 305.4 units per mg.

Our improved process may be applied to the synthesis of human calcitonin in a similar manner to that described in connection with salmon calcitonin. Human calcitonin includes 32 amino acids in its amino acid chain. The process begins by coupling proline, the amino acid at position 32 of the sequence, with a benzyhydrylamine resin followed by one by one addition of the other amino acids in sequence using the amino acid derivatives given in Table IV. When the amino acid sequence is completed, two types of peptides are obtained, depending on the choice of the cysteine derivatives used in Cycle 1 of the process. These two types of peptides may be written as:

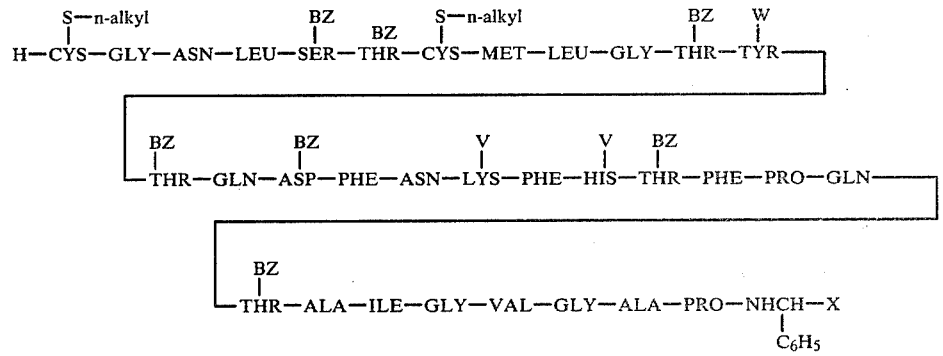

-continued

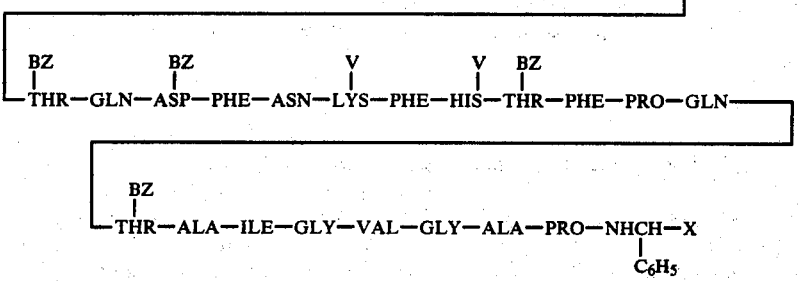

After treatment with acid to remove the resin support and acid labile groups, the peptides become:

Methylene chloride—two minutes
Chloroform—two minutes two times each

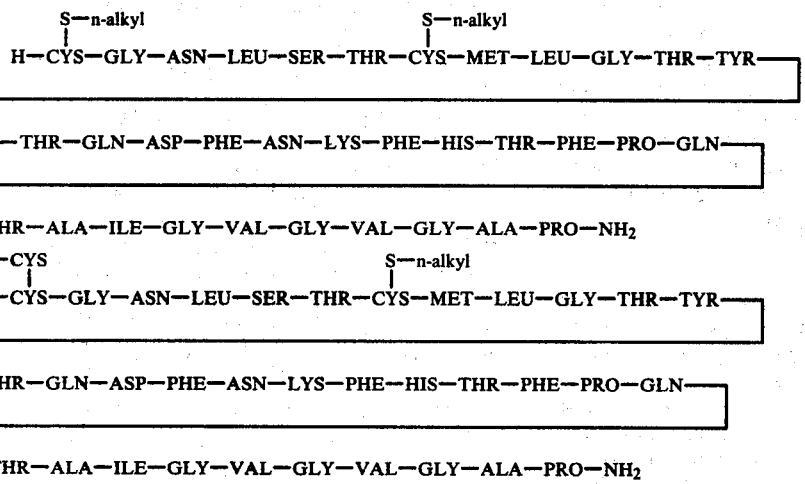

After these peptides have been allowed to rearrange under conditions as described herein for disulfide bond rearrangement, the peptide becomes the structure shown:

10% Triethylamine in chloroform—five minutes two times each
Chloroform—two minutes
Methylene chloride—two minutes three times each

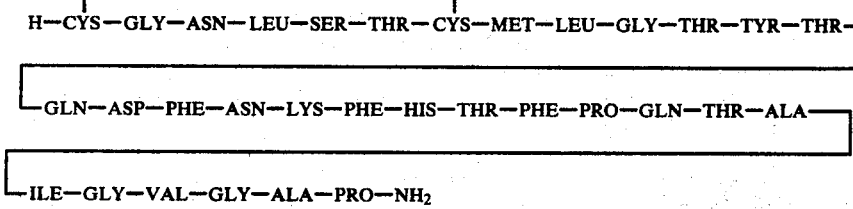

which is the structure of human calcitonin.

A specific example of the synthesis of human calcitonin using our improved process is given in Example III.

EXAMPLE III

Synthesis of Human Calcitonin

Resin Activation

The benzhydrylamine (BHA) resin (4 g) with an amine titer of 0.55 meq/g was placed in the reactor vessel of a peptide synthesizer marketed by Schwartz-Mann, Inc. of Orangeburg, N.Y. The resin was treated with 20 ml of the following solvents filtering after each treatment:

CYCLE 32

Coupling: The BHA resin, 20 ml of methylene chloride and 0.95 (0.0044 mole) of BOC-L-proline were agitated for 10 minutes. 4.4 ml of a methylene chloride solution of dicyclohexylcarbodiimide (1 millequivalent of DCCI per 1 ml of solution) was added to the reactor and the mixture agitated for 6 hours. The reaction mixture was removed from the reactor by filtration and the BOC-prolyl BHA resin subjected to the following successive 2 minute, 20 ml washes, removing the was by filtration each time:
Methylene chloride—two times
Methyl alcohol—two times Methylene chloride—two times Acetylation: The resin was then agitated with a mixture of 1.5 ml of triethylamine (TEA), 1 ml of acetic anhydride and 20 ml of chloroform for two hours. The reaction mixture was removed by filtration and the resin subjected to the following 2 minute, 20 ml washes;

Chloroform—two times
Methyl alcohol—two times
Methylene chloride—three times

A ninhydrin test was negative (E. Kaiser et al., Anal. Biochem., 34, 595-8 [1970].

Deprotection: The BOC-protected resin was agitated for 5 minutes with a mixture of 12.5 ml of trifluoroacetic acid (TFA) and 12.5 ml of methylene chloride. This mixture was removed by filtration and the resin was agitated with a second mixture of 12.5 ml of TFA and reaction mixture was removed by filtration and the resin subjected to the following 20 ml washes:

Methylene chloride—2 times two minutes each
Methyl alcohol—2 times two minutes each
Chloroform—2 times two minutes each
10% TEA in chloroform—2 times ten minutes each
Chloroform—2 times two minutes each
Methylene chloride—2 times two minutes each The L-proline BHA resin was titrated to establish the amino or proline titer. This value was 0.494 milliequivalents of amine or proline per gram of resin.

CYCLE 31

Coupling: The L-prolyl resin, 20 ml of methylene chloride and 0.83 g (0.0044 mole) of BOC-alanine were agitated for 10 minutes. The 4.4 ml of a methylene chloride solution of dicyclohexycarbodiimide (1 milliequivalent of DDCI per 1 ml of solution or a total of 0.0044 mole of DDCI) was added to the reactor and the mixture agitated for 2 hours. The reaction mixture was removed from the reactor by filtration and the BOC-L-alanyl-L-prolyl BHA resin subjected to the following successive 2 minute, 20 ml washes, removing the wash by filtration each time:

Methylene chloride—two times
Methyl alcohol—two times
Methylene chloride—three times A ninhydrin test was negative.

CYCLES 30 Through 26

The coupling and deprotection procedures used in these cycles were the same as in Cycle 31 except that the following amino acid derivatives were used in place of the alanine derivative:

Cycle 30—0.77 g (0.0044 mole) of BOC-glycine
Cycle 29—0.95 g (0.0044 mole) of BOC-L-valine
Cycle 28—The material used was the same as Cycle 30
Cycle 27—1.02 g (0.0044 mole) of BOC-L-isoleucine
Cycle 26—The material used was the same as Cycle 21

CYCLE 25

Coupling: The peptide resin obtained from Cycle 26 was washed twice with 20 ml portions of dimethylformamide (DMF). The resin peptide was then agitated for 10 minutes with a mixture of 2.04 g (0.0066 mole) of BOC-O-benzyl-L threonine and 20 ml of DMF. The 6.6 ml of DCCI in methylene chloride (equivalent to 0.0066 mole of DCCI) was added and the mixture agitated for 6 hours. The reaction mixture was removed by filtration. The resin peptide was subjected to two minute washes with two successive 20 ml portions of the following solvents: DMF, methylene chloride, methyl alcohol, methylene chloride. The ninhydrin test was negative.

Deprotection: Repeat deprotection procedure used in Cycle 32.

CYCLE 24

Coupling: The peptide resin obtained from Cycle 25 was washed twice with 20 ml portions of DMF. The resin was then agitated for 24 hours with a solution of 2.42 g (0.0066 mole) of BOC-L-glutamine-p-nitrophenyl ester in 25 ml of DMF. The reaction mixture was filtered and the resin peptide subjected to two minute washes with two successive 20 ml portions of the following solvents: DMF, methylene chloride, methanol, methylene chloride. Each individual solvent was removed by filtration. A ninhydrin test was negative.

Deprotection: The deprotection procedure used in Cycle 32 was repeated.

CYCLE 23

Coupling: The peptide resin obtained from Cycle 24 was agitated for 10 minutes with 1.42 g (0.0066 mole) of BOC-L-proline and 20 ml of methylene chloride. 6.6 ml of DCCI in methylene chloride (equivalent to 0.0066 mole of DCCI) was added and the mixture agitated for 16 hours. The reaction mixture was removed by filtration and the resin peptide was subjected to two minute washes with two successive 20 ml portions of the following solvents: methylene chloride, methyl alcohol, methylene chloride. Each individual wash was removed by filtration. The ninhydrin test was negative.

Deprotection: The deprotection procedure used in Cycle 32 was repeated.

CYCLE 22

The coupling and deprotection procedure used in this cycle were the same as in Cycle 23 except that in the coupling reaction., 1.75 g (0.0066 mole) of BOC-L-phenylalanine was used in place of BOC-L-proline.

CYCLES 21 through 18

The coupling and deprotection procedures used in these cycles were the same as in Cycle 31 except that the following amino acid derivatives were used in place of the alanine derivative:

Cycle 21—1.36 g (0.0044 mole) of BOC-O-benzyl-L-threonine
Cycle 20—1.71 g (0.0044 mole) of BOC-N (im)-carbobenzyloxy-L-histidine
Cycle 19—1.17 g (0.0044 mole) of BOC-L-phenylalanine
Cycle 18—1.67 g (0.0044 mole) of BOC-ε-carbobenzyloxy-L-lysine

CYCLE 17

The coupling and deprotection procedure used in this cycle were the same as in Cycle 24 except that 2.33 g (0.0066 mole) of BOC-L-asparagine-p-nitrophenyl ester was used in place of the glutamine derivative.

CYCLES 16 and 15

The coupling and deprotection procedures used in these cycles were the same as in Cycle 31 except that the following amino acid derivatives were used in place of the alanine derivative:

Cycle 16—1.17 g (0.0044 mole) of BOC-L-phenylalanine

Cycle 15—1.42 g (0.0044 mole) of BOC-L-aspartic acid-β-Benzyl ester

CYCLE 14

Same as cycle 24.

CYCLE 13

Same as Cycle 21

CYCLE 12

The coupling and deprotection procedures used in this cycle were the same as in Cycle 25 except that 2.45 g (0.0066 mole) of BOC-O-benzyl-L-tyrosine was used in place of the threonine derivative and the agitation time was extended to 16 hours.

CYCLE 11

Same as Cycle 25

CYCLES 10 through 17

The coupling and deprotection procedures used in these cycles were the same as in Cycle 31 except that in the coupling reaction the following amino derivatives wer used in place of the BOC-L-alanin.
Cycle 10—0.77 g (0.0044 mole) of BOC-glycine
Cycle 9—1.02 g (0.0044 mole) of BOC-L-leucine
Cycle 8—1.1 g (0.0044 mole) of BOC-L-methionine
Cycle 7—1.5 g (0.0044 mole) of BOC-S-3,4 dimethylbenzyl-L-cysteine CYCLES 5 and 4

The coupling and deprotective procedures used in these cycles were the same as in Cycle 31 except that in the coupling reaction the following amine derivatives were used in place of the BOC-L-alanine:
Cycle 5—1.3 g (0.0044 mole) of BOC-O-benzyl-L-serine
Cycle 4—1.02 g (0.0044 mole) of BOC-L-leucine

CYCLE 3

Same as Cycle 17

CYCLE 2

The coupling and deprotection procedures used in Cycle 2 were the same as in Cycle 31 except that in the coupling reaction the following amino acid derivative was used in place of the BOC-L-alanine:
0.77 g (0.0044 mole) of BOC-glycine.

CYCLE 1

The coupling and deprotection procedures used in these cycles were the same as in Cycle 31 except that in the coupling reaction the following amino acid derivatives were used in place of the BOC-L-alanine.
1.24 g (0.0044 mole) of BOC-S-ethylthio-L-cysteine After completion of Cycle 1, the resin peptide was washed with two successive 20 ml portions of n-hexane. The peptide material was removed from the reactor and dried in an electric vacuum oven at 40° C. and 0.1 mm of Hg for 24 hours. The blocked human calcitonin peptide resin weighed 10.3 g.

Cleavage with Hydrogen Fluoride

The dried resin peptide (2 g) and 21 ml of anisole were placed in a Teflon reaction vessel. The vessel equipped with a Teflon-coated magnetic stirrer was placed in a dry-ice bath and 15 ml of hydrogen fluoride and was condensed into the vessel. This mixture was stirred at 0° C. in an ice bath of 1 hour. The hydrogen fluoride was removed by evaporation at reduced pressure. The residue was triturated with 2×25 ml portions of ehtyl acetate. The peptide was extracted from the resin beads with 2×50 ml of glacial acetic acid. The extract was lyophilized to give the cleaved peptide.

Cyclization of Peptide to Human Calcitonin

The crude peptide 1000 mg was dissolved in 250 ml of oxygen-free distilled water with 1 ml of glacial acetic acid added. The pH of the solution was adjusted to 7.5 by the additional concentrated ammonium hydroxide. This mixture was stirred in a closed vessel under a stream of nitrogen for 24 hours. The pH of the reaction mixture was adjusted to 3.2 by the addition of glacial acetic acid. Lyophilization gave a solid product.

Purification of the Crude Human Calcitonin

The solid product was dissolved in 0.5 N acetic acid and purified by passing through a Sephadex G-25 (fine) gel-filtration column and eluted with 0.5 N acetic acid. The human calcitonin fraction from this column was collected and lyophilized to give a white fluffy solid.

This white fluffy solid was dissolved in 0.05 M aqueous ammonium acetate (pH 5). The solution was adjusted to pH 5 and purified by ion-exchange chromatography using a SP-Sephadex C-25 column eluted with ammonium acetate buffer. The human calcitonin fraction was collected and lyophilized twice to give a fluffy white solid. This material was found to be biologically and chemically equivalent to the product reported in the literature (Sieber, P., et al., Helv. Chim. Acts, 53, 2135–50 (1970). The biological activity was found to be 110 MRC units per mg.

Likewise, our improved process may be applied in the synthesis of vasopressin using as the reactants in the amino acid chain the groups set forth in Table V or equivalent thereof. The formulas of the two types of peptides resulting from the use of the amino acid derivatives described in Table V and before acid cleavage to remove the resin and acid labile blocking groups may be written as follows:

Type 1

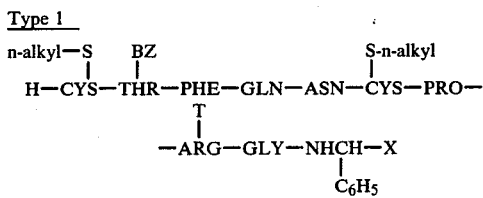

Type 2

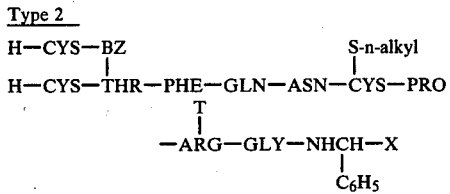

After acid treatment of these peptides to cleave the resin and acid labile protective groups, the formuli may be written:

Type 1

-continued

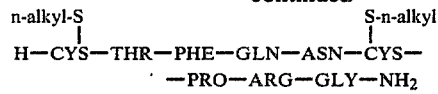

Type 2

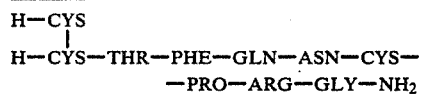

which are precursors of vasopressin.

After subjecting these peptides to our disulfide bond rearrangement procedure as herein described, the peptide becomes:

H—CYS—THR—PHE—GLN—ASN—CYS—
                              —PRO—ARG—GLY—NH₂ which is vasopressin.

To apply the improved process in the synthesis of porcine calcitonin, the amino acid chain for porcine calcitonin may be built using the reactants set forth in Table VI or equivalent thereof. The Type 1 and Type 2 formuli of the peptides resulting from the use of the amino acid derivatives described in Table VI, and before acid removal of the resin and acid labile protecting groups, may be written:

Type 1

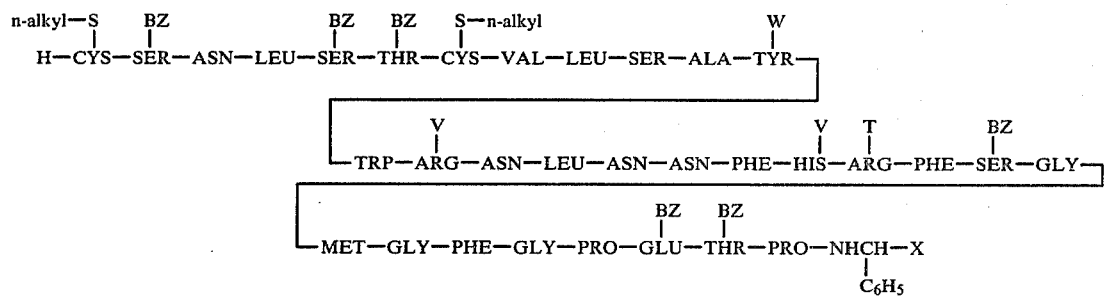

Type 2

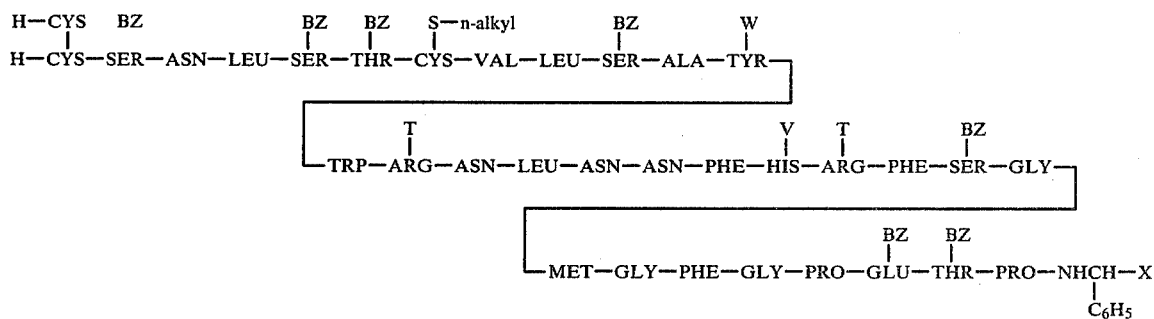

After acid treatment to remove all acid labile protecting groups, the peptides become:

Type 1

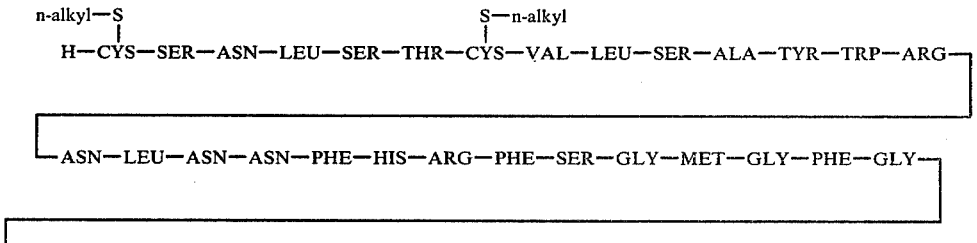

Type 2

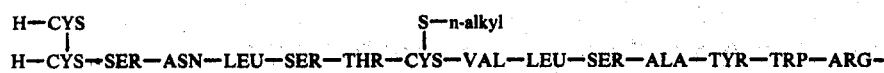

which are precursors of procine calcitonin.

After subjecting these peptides to our disulfide bond rearrangement procedure as herein described, the peptides become:

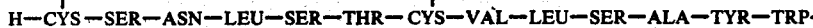

which is porcine calcitonin.

To apply the improved process in the synthesis of bovine calcitonin, the amino acid chain for bovine calcitonin may be built using the amino acid derivatives set forth in Table VII or equivalents thereof. The formuli for the two types of peptides resulting from the derivatives listed in Table VII and before acid cleavage, may be written:

Type 1

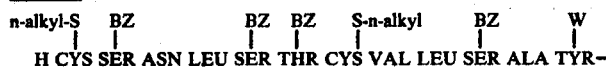

Type 2

After anhydrous treatment of these peptides to cleave the resin and the acid labile protective groups, the formuli become:

Type 1

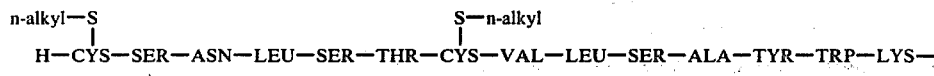

Type 2
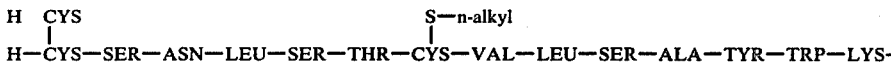
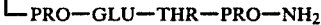

which are precursors of bovine calcitonin.

After subjecting these peptides to our disulfide bond rearrangement procedure as herein described, the peptides become:

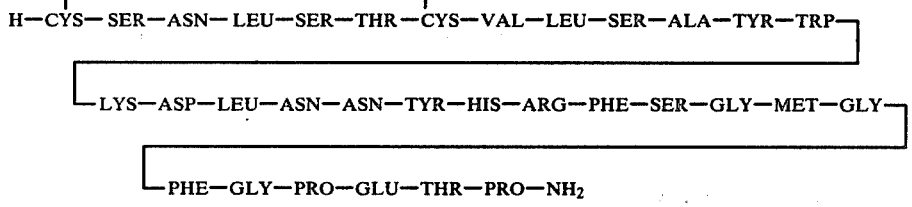

which is bovine calcitonin.

In the synthesis of eel calcitonin, the amino acid sequence of eel calcitonin may be prepared by using the amino acid derivatives set forth in Table VIII or equivalents thereof. The formuli for the two types of precursor resin peptides resulting from use of the derivatives listed in Table VIII and before acid cleaveage may be written:

Type 1
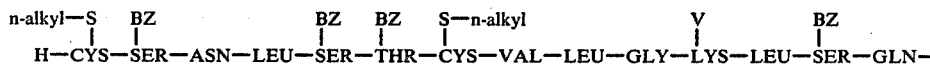
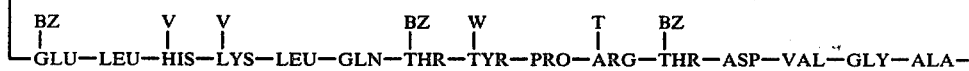
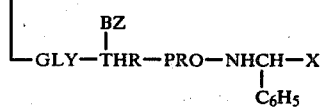

Type 2
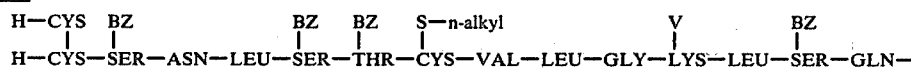
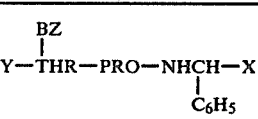

After anhydrous acid treatment of these peptides to cleave the resin and the acid labile protective groups, the formuli become:

Type 1

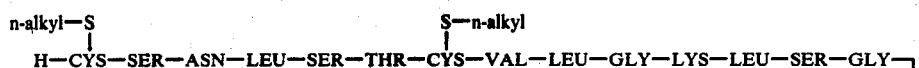
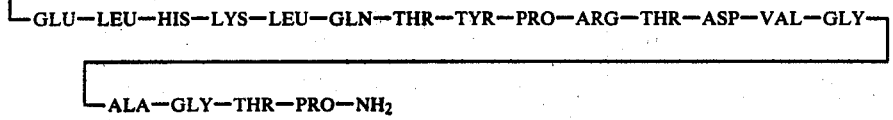
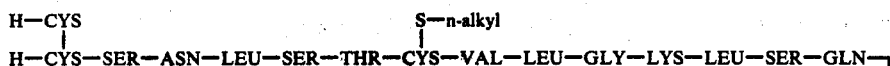

Type 2

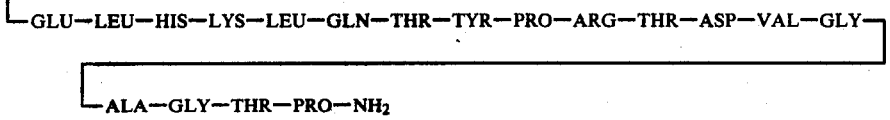

which are precursors of eel calcitonin.

After subjecting these peptides to our disulfide bond rearrangement procedure as herein described, the peptides become:

H-CYS-SER-ASN-LEU-SER-THR-CYS-VAL-
LEU-GLY-LYS-LEU-SER-GLN
GLU-LEU-HIS-LYS-LEU-GLN-THR-TYR-
PRO-ARG-THR-ASP-VAL-GLY
ALA-GLY-THR-PRO-NH$_2$

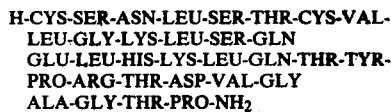

which is eel calcitonin.

In the synthesis of somatostatin, the amino acid sequence of somatostatin may be prepared using the amino acid derivatives described in Table IX or equivalents thereof. The formuli for the precursor resin peptide resulting from the use of the derivatives listed in Table IX and before acid cleavage may be written:

After anhydrous acid treatment to cleave the resin and acid labile protective groups, the formuli becomes:

which is a precursor of somatostatin.

After subjecting this peptide to our disulfide bond rearrangement procedure as herein described, the peptide becomes:

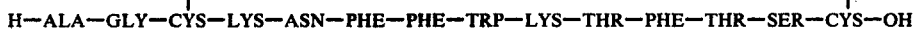

which is somatostatin.

While the invention has been specifically described and demonstrated with respect to specific peptides, it will be apparent to those skilled in this art that the invention is applicable to numerous specific peptide structures, and that the invention may be varied and changed in many ways all within the spirit of the invention and within the scope of the appended claims.

What is claimed is:

1. In a process for preparing a peptide having a disulfide ring structure, the step of holding a peptide having in its amino acid chain two cysteine residues, one of which has an n-alkylthio group attached thereto, and the other of which has attached thereto an n-alkylthio group or, if said other residue is at the amino terminal position, a cysteine group, in a solution substantially free of oxygen until rearrangement has taken place, to yield a cyclic disulfide peptide.

2. A process as set forth in claim 1 in which said solution is an aqueous solution.

3. A process as set forth in claim 1 in which said solution is an aqueous alcoholic solution.

4. A process as set forth in claim 2 which includes the step of agitating said solution during said rearrangement.

5. A process as set forth in claim 1 including conducting said rearrangement under a stream of innert gas.

6. A process as set forth in claim 5 wherein said gas is nitrogen.

7. A process as set forth in claim 5 which includes continuing the process for a period of at least one hour.

8. A process as set forth in claim 1 in which said peptide is:

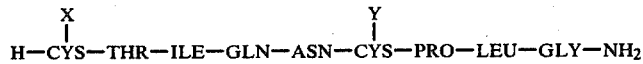

H—CYS—THR—ILE—GLN—ASN—CYS—PRO—LEU—GLY—NH₂ (with X on first CYS, Y on second CYS)

in which
Y is n-alkylthio and
X is n-alkylthio or H-CYS.

9. A process as set forth in claim 1 in which said peptide is:

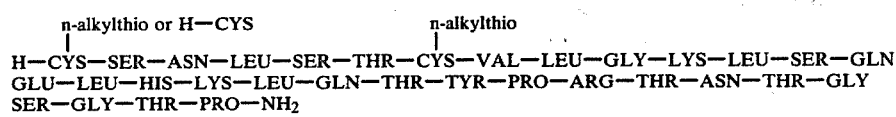

H—CYS—SER—ASN—LEU—SER—THR—CYS—VAL—LEU—GLY—LYS—LEU—SER—GLN
GLU—LEU—HIS—LYS—LEU—GLN—THR—TYR—PRO—ARG—THR—ASN—THR—GLY
SER—GLY—THR—PRO—NH₂

10. A process as set forth in claim 1 in which said peptide is:

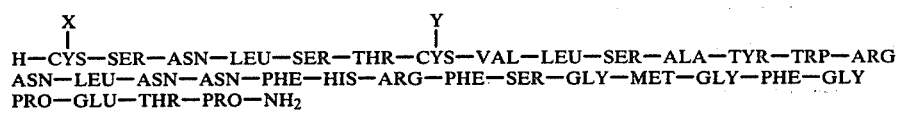

H—CYS—SER—ASN—LEU—SER—THR—CYS—VAL—LEU—SER—ALA—TYR—TRP—ARG
ASN—LEU—ASN—ASN—PHE—HIS—ARG—PHE—SER—GLY—MET—GLY—PHE—GLY
PRO—GLU—THR—PRO—NH₂ in which
Y is n-alkylthio and
X is n-alkylthio or H-CYS.

11. A process as set forth in claim 1 in which said peptide is:

H—ALA—GLY—CYS—LYS—ASN—PHE—PHE—TRP—LYS—THR—PHE—THR—SER—CYS—OH in which
X is n-alkylthio
Y is n-alkylthio.

12. A process as set forth in claim 1 in which said peptide is:

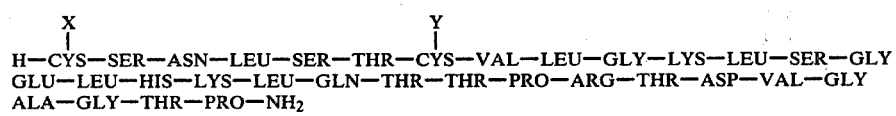

H—CYS—SER—ASN—LEU—SER—THR—CYS—VAL—LEU—GLY—LYS—LEU—SER—GLY
GLU—LEU—HIS—LYS—LEU—GLN—THR—THR—PRO—ARG—THR—ASP—VAL—GLY
ALA—GLY—THR—PRO—NH₂ in which
X is n-alkylthio or H-CYS and
Y is n-alkylthio.

13. A peptide having an amino acid sequence the same as that of a natural calcitonin and which has in said sequence a cysteine moiety protected by an n-alkylthio group and another cysteine moiety protected by an n-alkylthio group, or if said other moiety is in an amino terminal position, protected by another cysteine group.

14. A peptide as set forth in claim 13 in which each of said groups is an n-alkylthio group.

15. A peptide as set forth in claim 13 in which one of said cysteine moieties is in an amino terminal position and is cysteine.

16. A peptide as set forth in claim 13 in which said amino acid sequence is the same as that of a salmon calcitonin.

17. A peptide as set forth in claim 13 in which said amino acid sequence is the same as that of a porcine calcitonin.

18. A peptide as set forth in claim 13 in which said amino acid sequence is the same as that of somatostatin.

19. A peptide as set forth in claim 13 in which amino acid sequence is the same as that of an eel calcitonin.

* * * * *